United States Patent
Shpigelmacher et al.

(10) Patent No.: US 12,194,264 B2
(45) Date of Patent: Jan. 14, 2025

(54) MAGNETOMECHANIC TRIGGERING OF PAYLOAD RELEASE FROM MINIATURIZED DEVICES

(71) Applicant: BIONAUT LABS LTD., Herzliya (IL)

(72) Inventors: Michael Shpigelmacher, Los Angeles, CA (US); Alex Kiselyov, San Diego, CA (US); Suehyun Cho, Los Angeles, CA (US); Hovhannes Sargsyan, North Hollywood, CA (US)

(73) Assignee: BIONAUT LABS LTD. (IL)

( * ) Notice: Subject to any disclaimer, the term of this patent is extended or adjusted under 35 U.S.C. 154(b) by 748 days.

(21) Appl. No.: 17/289,682

(22) PCT Filed: Oct. 31, 2019

(86) PCT No.: PCT/US2019/059135
§ 371 (c)(1),
(2) Date: Apr. 28, 2021

(87) PCT Pub. No.: WO2020/092750
PCT Pub. Date: May 7, 2020

(65) Prior Publication Data
US 2021/0402161 A1 Dec. 30, 2021

Related U.S. Application Data

(60) Provisional application No. 62/754,998, filed on Nov. 2, 2018.

(51) Int. Cl.
*A61K 9/00* (2006.01)
*A61M 31/00* (2006.01)
*A61M 37/00* (2006.01)

(52) U.S. Cl.
CPC ....... *A61M 37/0069* (2013.01); *A61K 9/0009* (2013.01); *A61K 9/0024* (2013.01); *A61K 9/0097* (2013.01); *A61M 31/002* (2013.01)

(58) Field of Classification Search
CPC ................ A61K 9/0009; A61K 9/0024; A61K 47/6903; A61K 9/5094; A61M 37/0069;
(Continued)

(56) References Cited

U.S. PATENT DOCUMENTS

| 5,170,801 A | 12/1992 | Casper et al. |
| 8,369,942 B2 * | 2/2013 | Hyde .................... A61N 1/303 |
| | | 604/20 |

(Continued)

FOREIGN PATENT DOCUMENTS

| EP | 1 669 026 A1 | 6/2006 |
| EP | 2 303 226 B1 | 3/2016 |

(Continued)

OTHER PUBLICATIONS

International Preliminary Report on Patentability dated May 14, 2022 in respect of International PCT Application No. PCT/US19/59135.
(Continued)

*Primary Examiner* — Deanna K Hall
(74) *Attorney, Agent, or Firm* — Mark S. Cohen; PEARL COHEN ZEDEK LATZER BARATZ LLP

(57) ABSTRACT

A carrier device and methods of use are described. The device and methods are directed toward implanting in biological tissue and for releasing a medical payload or functional material in biological tissue according to a remote magnetic trigger. The carrier device has a cavity with an opening through an external surface of the device. The carrier device includes at least one moveable, magnetic element sensitive to a magnetic field gradient. When a magnetic field gradient, rotating magnetic field, or uniform magnetic field, or a combination of thereof is applied to the tissue, the moveable magnetic element provides release of the medical payload or functional material through the
(Continued)

cavity opening. In some embodiments, payload release can be started, stopped, and restarted at a later time or place. In addition to payload release, devices of this invention are equipped with a propelling element, the propelling element is responsive to external stimuli that enables propulsion and navigation of the device.

24 Claims, 3 Drawing Sheets

(58) Field of Classification Search
CPC ............ A61M 31/002; A61M 5/14276; A61M 2205/8287; A61M 2205/3515
See application file for complete search history.

(56) References Cited

U.S. PATENT DOCUMENTS

| | | |
|---|---|---|
| 2004/0050394 A1 | 3/2004 | Jin |
| 2004/0076602 A1* | 4/2004 | Harris .................... A61K 47/10 |
| | | 525/54.1 |
| 2004/0106914 A1 | 6/2004 | Coppeta et al. |
| 2005/0055014 A1 | 3/2005 | Coppeta et al. |
| 2006/0165751 A1 | 7/2006 | Chudzik et al. |
| 2010/0121422 A1 | 5/2010 | Jolly et al. |
| 2013/0030354 A1* | 1/2013 | Chin .................... A61K 9/0097 |
| | | 604/20 |
| 2013/0096503 A1* | 4/2013 | Haase ............... A61M 5/14276 |
| | | 604/152 |
| 2013/0303847 A1 | 11/2013 | Sitti et al. |
| 2014/0142556 A1* | 5/2014 | Kuo ..................... A61M 5/168 |
| | | 604/408 |
| 2015/0001187 A1 | 1/2015 | Amoako-Tuffour et al. |
| 2015/0064241 A1 | 3/2015 | Conrad |

FOREIGN PATENT DOCUMENTS

| | | |
|---|---|---|
| JP | H03-146031 A | 6/1991 |
| JP | 2004-520088 A | 7/2004 |
| JP | 2011-526288 A | 10/2011 |
| JP | 2017-158603 A | 9/2017 |
| WO | WO 99/33513 | 7/1999 |
| WO | WO-2010/054281 A | 5/2010 |

OTHER PUBLICATIONS

Office Action dated Jul. 5, 2022 in respect of Japanese Patent Application No. 2021-523360 with English Translation thereof.
English Translation of Notice of Allowance dated Oct. 4, 2022 in respect of Japanese Patent Application No. 2021-523360.
Partial Supplementary EP Search Report dated Jun. 29, 2022 in respect of EP Application No. 19880749.7.
Extended EP Search Report dated Oct. 12, 2022 in respect of EP Application No. 19880749.7.
International Search Report dated Jan. 22, 2020 from corresponding International PCT Application No. PCT/US19/59135.

* cited by examiner

MAGNETOMECHANIC TRIGGERING OF PAYLOAD RELEASE FROM MINIATURIZED DEVICES

CROSS-REFERENCE TO RELATED APPLICATIONS

This application is a U.S. national stage application under 37 U.S.C. 371 of PCT International Application PCT/US2019/059135, filed Oct. 31, 2019, which claims benefit of U.S. Provisional Application No. 62/754,998 filed Nov. 2, 2018, the priority dates of which are hereby claimed, and the contents of each of which are hereby incorporated by reference in their entireties.

BACKGROUND

Methods currently exist to remotely trigger release of a medical payload, such as drugs and diagnostic aids, from particles or devices implanted in living tissue. The purpose of such methods is to generate an external trigger for payload release (drug or diagnostics) from a carrier (e.g., particle or implantable device) housing such a payload in living tissue. Remotely-triggered payload release is desirable in supporting specific clinical goals, such as:

Release of a medical payload only when the carrier particle is in the right location for treatment (e.g., a tumor);

Release of a medical payload only when the moment is right (e.g., in the middle of a clinical procedure); or Release of a medical payload in a time-dependent or stop-and-go manner to treat predetermined area(s) for a predetermined time.

Existing triggering methods rely on a variety of effects, including:

Thermal/mechanical effects based on cavitation (leading to localized heating due to vibration and increased speed of diffusion and/or changes in localized chemical characteristics which increase diffusion);

Mechanical degrading/rupturing of carrier leading to payload release;

Shape change of the carrier or an integrated part thereof; or

Change to the characteristics of the surrounding biological tissue into which the payload is being released (e.g., sonoporation), resulting in improved payload diffusion/absorption through tissue.

A common drawback of these methods is that each method supports only a subset of the typical technical features desired from a clinical standpoint. These features for a remote trigger system for clinical payload release include:

Customizable tissue penetration depth (10 cm or greater).

Support for gradual payload release over a controllable time period, or an on-off switchable release functionality (rather than a single release pulse). For example, methods relying on degradation of a uniform polymer encasing the payload are by design irreversible and do not have gradual release functionality; and Individual control of multiple payload carriers in a single tissue volume unit (e.g., releasing payload selectively from only a single particle out of many located within the same organ). Existing methods do not offer this functionality.

It would therefore be desirable to have implantable devices and methods thereof, which overcome the above restrictions of the current capabilities This goal is attained by embodiments of the present invention.

SUMMARY

According to various embodiments of the present invention, there is provided an implantable payload carrier device. The carrier device has a cavity with an opening through an external surface of the device. The carrier device includes at least one moveable, magnetic element sensitive to a magnetic trigger. When the magnetic trigger is applied to the tissue, the moveable magnetic element provides release of the medical payload or functional material through the cavity opening.

In certain embodiments, the magnetic trigger used to release the medical payload is controlled via a magnetic gradient, uniform magnetic field changing its direction in space, presence/absence of a magnetic signal or a combination of thereof. Some embodiments of the present invention rely on magnetic fields for remote triggering and navigation of carriers implanted in living tissue. Other embodiments combine magnetic field gradients with other external physical stimuli, non-limiting examples of which include: ultrasound, piezoelectric, optical (e.g., near infrared (NIR)), electromagnetic field phenomena and effects; and thermodynamic phenomena and effects, including both temperature and pressure effects.

The terms "carrier device" and "carrier" herein denote an object that is implantable in biological tissue, and capable of carrying and releasing a medical payload into the tissue. The term "device" or the term "particle" are also used to describe a carrier or a carrier device. The term "medical payload", or equivalently the term "payload" used in a medical context is understood herein to include any substance or material of a medically-therapeutic or diagnostic nature. In certain embodiments, a medical payload or payload is equivalent to a "functional material" wherein the function is related to or directed toward treatment or for diagnostic purposes. The term "device" (with reference to a carrier) herein denotes a carrier which is fabricated by manufacturing techniques, including, but not limited to, lithography, thin-film technologies, deposition technologies, etching, coating, molding, self-assembly, chemical synthesis and the like.

In certain embodiments of the present invention, carrier devices are miniaturized for implantation in biological tissues. The term "miniaturized" (with reference to a carrier) herein denotes a carrier of small size, including, but not limited to: carriers of millimeter to centimeter scale; carriers of micrometer ("micron") scale, referred to as "carrier micro-devices"; carriers of nanometer scale referred to as "carrier nano-devices." Not only are the carriers themselves of the size scales indicated above, but the carriers' individual components are also of comparable scale. It is to be noted that certain carrier dimensions can be of different scales, e.g., a carrier may have one dimension in the nanometer range and another dimension in the micrometer range. All such miniatured devices are included in embodiments of this invention.

In one embodiment, this invention provides a carrier device for implanting in a biological tissue to release a medical payload or functional material in the tissue or in another tissue, the carrier device comprising:

a cavity having an opening through an external surface of said device;

a matrix comprising a medical payload or a functional material, where the matrix is contained within the cavity, representative examples of a matrix include but not limited to hydrogels, polycaprolactone, (poly)ethyleneglycols, glycinebetaine, alginates, collagen or collagen composites;

a magnetic component contained and moveable in the cavity, and is arranged so that, when a magnet trigger is applied, the magnetic component extrudes the matrix through the opening of cavity to be released into the tissue.

In one embodiment, this invention provides a carrier device for implanting in a biological tissue to release a medical payload or functional material in the tissue or in another tissue, the carrier device comprising:

a cavity having an opening through an external surface of said device; and a magnetic matrix comprising a medical payload or a functional material, where the matrix is contained within the cavity;

wherein the magnetic matrix is arranged so that, when a magnet trigger is applied, the matrix is extruded on its own through the opening of cavity to be released into the tissue. For example, the matrix comprises magnetic nanoparticles coated with the medical payload.

In one embodiment, this invention provides a carrier device for implanting in a biological tissue to release a medical payload or functional material in the tissue or in another tissue, the carrier device comprising:

a cavity having an opening through a surface of said device;

a matrix comprising a functional material, wherein the matrix is contained within said cavity, and a source of pressure inside the cavity pushes the matrix towards the cavity opening; and a rotatable magnetic cap covering the opening of the cavity and having one or more openings, and is arranged so that, when a magnet trigger is applied, the cap rotates so that the cavity opening is aligned with the opening(s) in the cap to release the matrix is extruded through the opening of cavity to be released into the tissue.

In one embodiment, the device further comprises a propelling component. In one embodiment, the propelling component is responsive to external stimuli. In one embodiment, the stimuli are selected from ultrasound (US), piezoelectric, magnetic, electric, electromagnetic, electromagnetic radiation or a combination thereof. In one embodiment, application of the stimuli to the propelling component propels the device. In one embodiment, the external stimulus is US. In one embodiment, the external stimuli comprise magnetic stimuli to propel the propelling component and other magnetic stimuli to release the functional material from said device or from components thereof. In some of these embodiments, of the cavity opening relative to the direction of magnetic propulsion of the carrier is oriented to avoid interference (i.e., the opening is in the back or orthogonal to direction of propulsion).

In one embodiment, this invention provides a system comprising:

a device as disclosed herein; and a remote unit;

wherein the remote unit is configured to apply external stimuli to said device.

In one embodiment, the external stimuli comprise magnetic stimuli. In one embodiment, the external stimuli comprise magnetic stimuli and ultrasound (US). In one embodiment, the external stimuli comprise magnetic/electric, electromagnetic or US stimuli to propel the device; or a combination thereof.

In one embodiment, this invention provides a method for releasing a medical payload or functional material in biological tissue, said method comprises:

inserting a device described herein into biological tissue;

applying a magnetic trigger to the device to release the matrix in the tissue.

In one embodiment, after inserting the device into the tissue, applying external stimuli to propel the device to a defined location within the tissue. In one embodiment the external stimuli comprise ultrasound (US), magnetic, electric, electromagnetic, piezoelectric, optical (e.g., near infrared (NIR)), electromagnetic radiation or a combination thereof. In one embodiment following application of the external stimuli, the functional material interacts with the tissue or with component(s) of/in the tissue. In one embodiment, the interaction results in a therapeutic effect, a diagnostic effect or a combination thereof. In one embodiment. the method further comprises imaging the location of the device within the tissue.

In one embodiment, this invention provides a method of treating a subject, the method comprises:

inserting a device described herein into the subject;

applying a magnetic trigger to the device to release the matrix in the subject.

In one embodiment, inserting the device comprises inserting the device into a certain tissue within the subject. In one embodiment, after inserting the device into the tissue applying external stimuli to propel the device to a defined location within the subject. In one embodiment the external stimuli comprise ultrasound (US), magnetic, electric, electromagnetic, piezoelectric, optical (e.g., near infrared (NIR)), electromagnetic radiation or a combination thereof. In one embodiment, following application of the external stimuli, the functional material interacts with the tissue or with component(s) of/in the tissue. In one embodiment, the interaction results in a therapeutic effect, a diagnostic effect or a combination thereof. In one embodiment. the method further comprises imaging the location of the device within said subject.

BRIEF DESCRIPTION OF THE DRAWINGS

The subject matter disclosed may best be understood by reference to the following detailed description when read with the accompanying drawings in which.

(b) When the vessel embedded in agar was brought closer to a large magnetic gradient, the stainless-steel sphere inside the vessel moves towards the gradient and extrudes hydrogel soaked with Rhodamine B. (c) After the initial extrusion occurred, the entire vessel was pushed further into the agar gel to simulate microbot movement to a different region. (d) At this new location, a second extrusion was performed and the remaining hydrogel was extruded upon incident magnetic field gradient.

Figure 4:
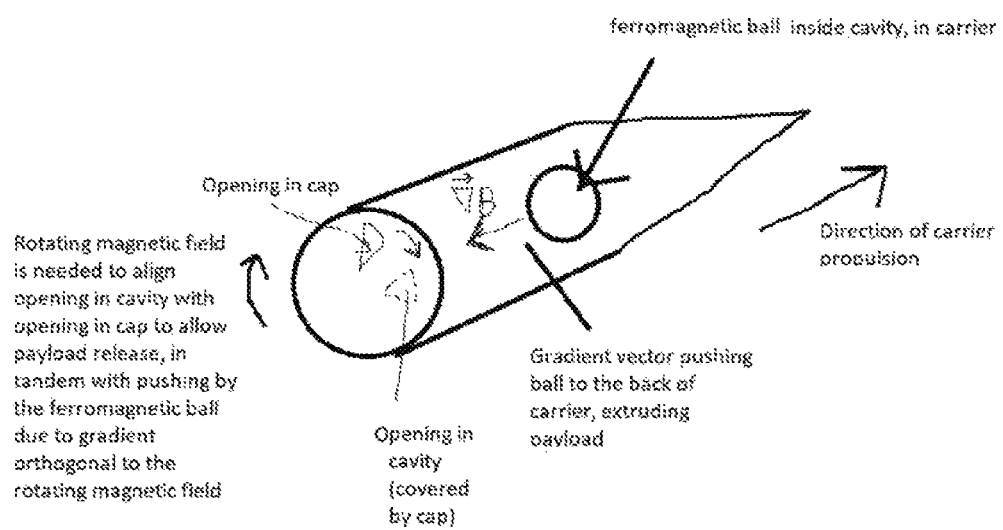

FIG. 4: depicts microparticles according to certain embodiments of the invention.

Figure 5:
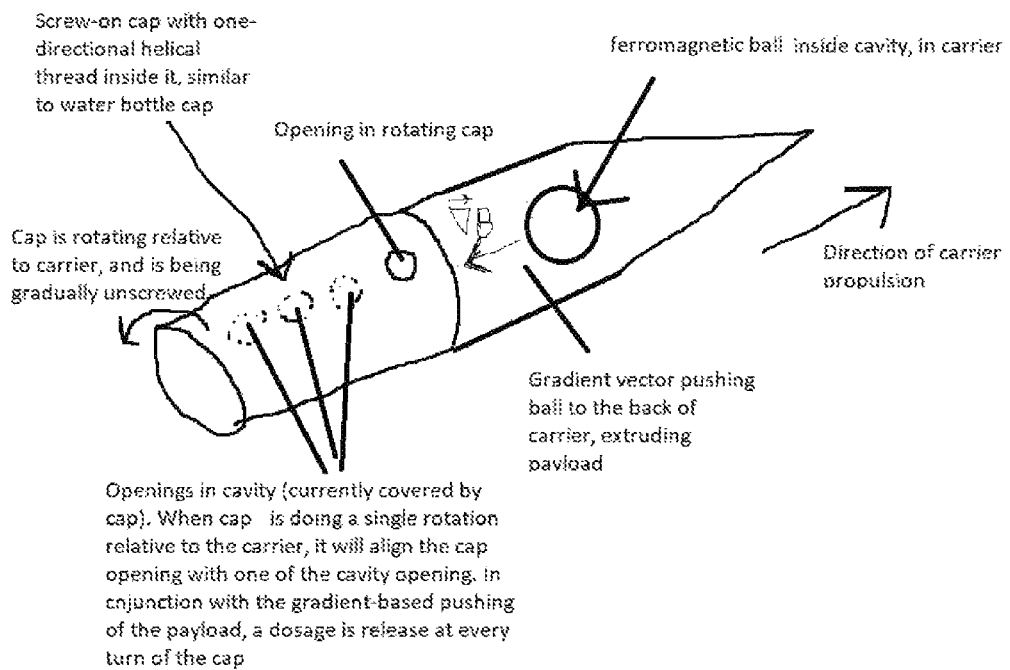

FIG. 5: depicts microparticles according to certain embodiments of the invention.

Figure 6:
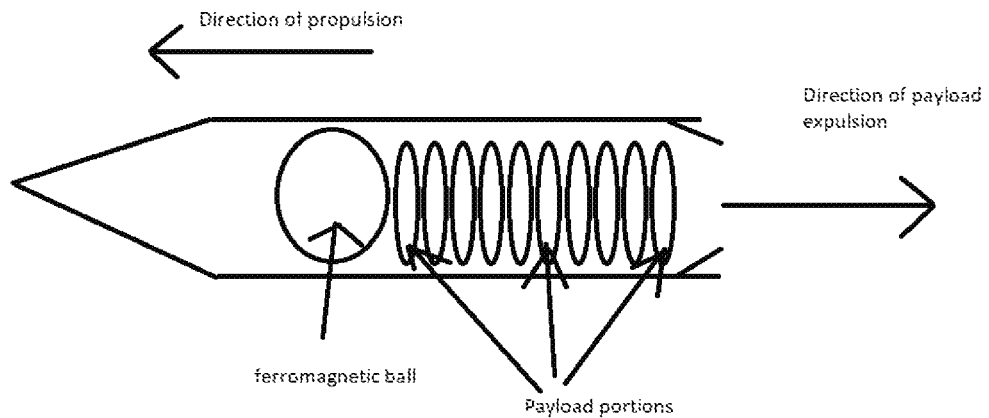

FIG. 6: depicts microparticles according to certain embodiments of the invention.

For simplicity and clarity of illustration, elements shown in the figures are not necessarily drawn to scale, and the dimensions of some elements may be exaggerated relative to other elements. In addition, reference numerals may be repeated among the figures to indicate corresponding or analogous elements.

DETAILED DESCRIPTION

Various embodiments of the present invention provide a carrier device containing a functional material or medical payload which is released from the carrier upon demand The term "functional material" includes a substance, compound or material of a medically-therapeutic or diagnostic nature. The functional material is released from the carrier when external stimuli are applied. The external stimuli can be electric, magnetic, electro-magnetic, electromagnetic radiation, (e.g., near infrared (NIR)), ultrasound, or a combination thereof. In some embodiments, the functional material is provided as part of a matrix, such as a hydrogel matrix.

According to various embodiments of the present invention, there is provided an implantable payload carrier device. The carrier device has a cavity with an opening through an external surface of the device. The carrier device includes at least one moveable, magnetic element sensitive to a magnetic trigger. When the magnetic trigger is applied to the tissue, the moveable magnetic element provides release of the medical payload or functional material through the cavity opening.

In certain embodiments, the magnetic trigger used to release the medical payload is controlled via a magnetic gradient, uniform magnetic field changing its direction in space, presence/absence of a magnetic signal or a combination of thereof.

In some embodiments, the cavity opening is sealed by or covered with a flexible seal, which opens when the matrix is extruded by the magnetic component. In some embodiments, the flexible seal closes when the magnetic trigger is removed. In some embodiments, the cavity opening is sealed by or covered with a flexible seal, which is a magnetic actuator (opening/closing in response to the external gradient or another magnetic trigger).

In some embodiments, the carrier has multiple cavities, each with a different mechano-magnetic configuration (e.g., different actuator size/membrane elasticity), so they can be controlled independently.

In certain embodiments, several magnetic field elements are used for payload release. For example, a cavity may have a ferromagnetic ball which pushes the payload towards the opening, in response to a magnetic gradient. In addition, the opening may be covered by a circular cap with an opening at a given location (similar to a salt container). The cap may or may not be a diametrically magnetized cap, and may or may not have a mechanical mechanism allowing it to rotate only in a given direction (clockwise or counter clockwise). Payload release will happen only when a gradient is applied towards the opening and the cap is partially or completely removed by rotation in the appropriate direction (clockwise/counter clockwise) relative to the main carrier body, to align the opening in the cavity with the opening in the cap. This creates a double safety mechanism and increases accuracy of control over payload release. See FIG. 4.

If propulsion is achieved using a rotating magnetic field, a magnetic gradient or a combination of the two, specific methods are needed to prevent interference between magnetic propulsion and payload release. These include stopping the carrier before applying an opposed gradient (for payload release), or rotating in the opposite direction for payload release vs. propulsion. A one-directional rotating cap may be used to ensure that the cap does not rotate relative to the body in response to a rotating magnetic field used for propulsion (e.g., clockwise). For example, the cap may be non-magnetic. A clockwise rotation of the main carrier body rotates the cap together with the carrier, not changing the alignment of the openings in cap and cavity. A counter-clockwise rotation of the carrier body rotates it relative to the cap, allowing alignment of the openings and payload release. This method allows more accurate control over payload release speed by controlling the rotation speed of the cap.

In certain embodiments, the opening of the cavity is orthogonal or opposite to the direction of magnetic propulsion of the carrier to avoid interference. One potential advantage of having the opening in the back (i.e., opposite to the direction of motion) is that the payload is extruded backwards to an area where the carrier device has already passed through (it is disturbed and is less dense tissue hence lower tissue pressure, making payload release easier).

In some embodiments, the built-in magnetic component for propulsion is located at a predefined distance from payload release actuator, to prevent interference via attraction of the payload release actuator to the magnetic component needed for propulsion. Basically, if the magnet used for propulsion is too close to the magnetic ball or other magnetic element used for payload extrusion, they can stick together and no payload extrusion will occur. In that case, they either need to be kept at a distance from each other or need to be shielded by a material used for magnetic shielding (e.g., Mu metal).

In certain embodiments, the cap and the cavity may contain several openings orthogonal or opposite to the direction of motion, where a rotation of the cap aligns the openings to allow release of a payload, via diffusion or in combination with gradient-based extrusion using another magnetic actuator in the cavity. See FIG. 5. For example, specific design of an opening pattern can yield a particular sequence of payload release pulses, one for each opening being exposed to the surrounding tissue with each turn of the cap.

In certain embodiments, the magnetic actuator inside carrier cavity is used to expel discrete portions of functional material (e.g. capsules/cartridges) by pushing them mechanically via the opening in the cavity, controlled by a magnetic gradient or another magnetic signal. See FIG. 6. The mechanism is similar to a "Newton cradle" device, where balls are stacked in a row touching each other. The momentum generated by a ball hitting the row on one side is transferred to the last ball on the other side, while the other balls in the middle remain stationary. Using this principle, in one embodiment, the original ball generating the impact is replaced by the magnetic actuator (inside the carrier cavity), while the row of balls is replaced by a row of discrete payload portions. The momentum generated by the magnetic actuator (e.g., a ferromagnetic ball inside cavity) travels through the entire row of payload portions and is transferred to the last portion of payload, which is expelled from the cavity via the opening. The opening may be covered with a flexible membrane or another mechanical mechanism (e.g., a small sloped lip) to prevent accidental escape of the payload portions during the carrier movement, except when pushed with enough momentum. To use this method efficiently, the magnetic stimulus to start the motion of magnetic actuator is applied in one direction (for the initial impact of the actuator with the payload portions row) and then reversed to the other direction to retract the actuator to its initial position. This is done by the current design, where a magnetic gradient towards the direction of propulsion yields motion forward, and reversal of the gradient to the back of the carrier activates the magnetic actuator inside the cavity, yielding payload release to the back, using the mechanism described above. To clarify, the method may require one or more magnetic gradient pulses to release a single portion from the cavity.

In certain embodiments, instead of a magnetic actuator inside the cavity, it is possible to place a permanent source of pressure inside the cavity (e.g., a spring) constantly pushing the payload towards one or more opening(s) in the cavity. Said cavity is covered by a twistable cap, with one or more openings. A single turn of the cap using a magnetic field (as described in other embodiments herein) aligns the openings in the cap with the opening in the cavity, and allows for release of payload from the cavity due to the consistently high pressure. The advantage of this method is that it no longer relies on a magnetic gradient to push the payload from the cavity, and the release can be controlled by a rotating magnetic field (even a uniform magnetic field), while dosage is controlled by the number of cap turns and mechanical alignment of openings in the cavity and the cap.

Other embodiments can combine rotating field, gradient field, uniform fields or a combination thereof to control the extrusion of a payload using increased pressure inside the cavity and opening/closing of cavity containing payload to allow payload release In some embodiments of the present invention, the carrier device and its component parts are miniaturized. The device and/or the structures included in the device have at least one dimension at the microscale, the nanoscale or a combination thereof. According to some embodiments, the diameter or actual length of the overall device is selected from: between 100 and 5,000 micrometers, between 10 and 100 micrometers, between 1 and 10 micrometers, between 200 and 1,000 nanometers, and any combination thereof. According to some embodiments, the diameter or actual length of the overall device is from 200 nanometers up to 5,000 micrometers.

In some embodiments of the present invention, a carrier device comprises a shape selected from elongated, axisymmetric, centrosymmetric, chiral, random or a combination thereof. In some embodiments of the present invention, the moveable magnetic element comprises a configuration selected from a sphere, an elongated shape, a strip, a sheet, a plug, a coil, a helix, arm, a joint and a combination thereof.

The embodiments shown in the above-referenced drawings and descriptions are non-limiting; other magnetic-sensitive configurations are also possible in keeping with the present invention. In particular, one or more moveable, magnetic responsive components of different shapes and materials may be located at different positions inside the cavity relying on the principles describe above to achieve the effect of payload release.

In one embodiment, this invention provides a method to manufacture payload carriers wherein the payload can be released based on an external magnetic trigger/stimulus of a predefined magnetic gradient, while potentially supporting remote-controlled motion of the carrier using an externally applied electromagnetic field. In one embodiment, the payload is or comprises functional material. In one embodiment, the particle is at halt when releasing the payload. In other embodiments, the particle is in motion while releasing the payload.

It is contemplated that carrier devices according to embodiments of the present invention will include particles described in International Patent Application PCT/US2018/030960 filed on May 3, 2018 and titled "METHODS AND SYSTEMS TO CONTROL PARTICLES AND IMPLANTABLE DEVICES," which is hereby incorporated by reference in its entirety. Briefly, such particles are microelectromechanical (MEM) carrier devices, which comprise: (i) an actuator; (ii) a responsive element; (iii) a sensor; and (iv) an electronic circuit; wherein: said actuator controls and operates said responsive element; said electronic circuit controls said actuator; and said sensor receives signals transmitted by a remote unit. It is also contemplated that carrier devices according to embodiments of the present invention will be included in the platforms described in International Patent Application PCT/US2018/030960. Briefly, such platforms comprise the following modules: (a) one or more carrier devices described herein and comprising embedded logic and various MEM components; (b) a delivery and/or retraction module, configured to deliver and/or retract the devices; (c) an external signal generator; (d) an imaging module, configured to monitor said particles; and (e) an integration module configured to receive inputs from and to provide output control commands to other modules; wherein: said modules are configured to interact/communicate with each other; and said modules are internally controlled, externally controlled or both; and wherein said platform provides active, pre-determined, fully controlled, precise delivery of said devices in vitro, in vivo, and/or in a patient.

For various applications, it may be beneficial to manufacture payload carriers (e.g., micro/nano particles) whose motion can be remotely controlled using an externally applied electromagnetic field. An example of such particles is described in U.S. Pat. No. 8,768,501, whose disclosure is incorporated herein by reference in its entirety. Such exemplified particles are magnetically-actuated propellers (MAPs). The propellers are structures with typical feature sizes in the range of 20 nm up to 100 microns in one spatial dimension. The MAPs can be produced in large numbers from nano-structures surfaces in one embodiment. The MAPs are propelled and controlled by magnetic fields. The MAPs form is a screw-like form. The screw-like MAPs are rotated and driven by a rotating magnetic field. Rotation of the MAPs around their long axis, propels them forward. A method of design for payload carriers is described below, which support such functionality, while also supporting the features summarized above pertaining to remote controlled payload release based on an ultrasound signal.

In some embodiments, the magnetic component comprises a ferromagnetic or paramagnetic material. The magnetic component can be a particle/structure made of a ferro/para-magnetic material, or it can be made of a non-ferro/non-para magnetic material that is coated by a ferro/ para magnetic coating layer. The ferro/para magnetic component may comprise a ferro/para magnetic portion and a non-ferro/non-para-magnetic portion attached to each other. In some embodiments, a ferro/para-magnetic coating layer on a non-ferro/non-para magnetic material coats at least a portion of the non-magnetic material, or coats the entire exposed surface of the non-magnetic material.

In embodiments where the ferromagnetic or paramagnetic particles are partially coated or are coating or are in contact with/by a non-magnetic material, non-limiting examples of such non-magnetic material include diamagnetic dielectric materials ($SiO_2$, alumina), diamagnetic metals (Cu, Ag, Au, Ti, Ti/Ni alloys) and diamagnetic organic coating (organic polymers, small molecules, a chiral compound etc.).

In some embodiments, the ferromagnetic portion or paramagnetic portion is or comprises a suitable ferromagnetic or paramagnetic substrate known in the art. In some embodiments the ferromagnetic portion comprises Co, Fe, Ni, Gd, Tb, Dy, Eu, oxides thereof, alloys thereof or mixtures thereof. In other embodiments the paramagnetic portion comprises magnetic doped semiconductors.

In a representative embodiment of this invention, particle (carrier device structure) sizes could vary between 20 nm and 5 mm In some embodiments, the devices are in the micrometer range. In some embodiments, the devices are in the nanometer range. Within a certain range means that the largest measured dimension of the device is within that range. Devices within the millimeter range are also part of this invention. Microdevices of this invention may possess dimensions in both the nanometer and in the micrometer range Millimeter range devices may possess dimensions in the mm, nm range or a combination thereof. Sizes (or largest dimension size of devices of this invention range between 20 nm and 100 nm, between 10 nm and 10 mm, between 20 nm and 1 mm, between 10 nm and 1 micron (micron=µm), between 10 nm and 10 microns, between 20 nm and 100 microns, between 1 micron to 10 microns, between 10 microns and 100 microns, between 100 microns and 1 mm, between 1 mm and 10 mm, between 1 micron and 5 mm, between 10 nm and 1 mm, between 100 nm and 1 micron, between 100 nm and 10 micron, between 100 nm and 100 micron, between 100 nm and 1000 microns. Compositions comprising particles of different sizes, different size ranges and a combination of particles of various/different sizes is included in embodiments of this invention.

In a representative embodiment of this invention, particle (carrier device structure) sizes could vary between 20 nm and 5 mm and exhibit a variety of geometries specifically selected to enhance their active, externally-induced transport through media of interest. Examples include transcellular or paracellular space, biological membranes, specific biologically and or disease-relevant barriers exemplified by hematoencephalic or peritumoral barriers, extracellular matrix, specific tissues, organs and/or blood/lymph vessels. Representative examples of shapes include but are not limited to helical (worm, screw-like), micro/nanopropellers, threads and/or ribbon-like, smooth, etched-surface sphere/spheroids, particles with or without one/multiple external appendage(s) as exemplified by cilia, flagellum/flagella, fin(s). Moreover, due to both the active transport of the particles and expeditious target, tissue and/or organ delivery, release of the payload and retraction of the particles, the particle-(in vivo) system interaction is carefully controlled, limited and unlikely to trigger unwanted physiological effect(s) as exemplified by immunological, inflammatory and/or metabolic responses. In order to further minimize potential in vivo side effects, a specific selection of biocompatible, non-toxic biodegradable polymers or a combination of thereof could be used. Representative polymers include but are not limited to polyvinylalcohol (PVA), polyethyleneglycol (PEG), poly (N-2-hydroxypropyl) methacrylamide, poly(N-isopropyl) acrylamide, polylactic acid, chitosan, and polyglycolide.

In summary, the embodiments described here provide actively navigated, tractable magnetic composite nano-microparticles to deliver and release a targeted payload at precise locations. Multiple specific factors, including physical parameters of the magnetic trigger and particle composition and geometry, are amenable to optimization to achieve selective, precise, safe and efficacious payload delivery to a target ex vivo or in vivo.

Magnetomechanic Release of Hydrogel-Payload Combination.

In this example, fabrication of a vessel that can transport and release a hydrogel matrix via a magnetomechanic mechanism is demonstrated. The vessel contains a ferromagnetic piston, which in the presence of an external magnetic gradient, travels outward towards the gradient while in the process extruding the hydrogel matrix out of the vessel. This demonstrates the possibility of controlled release of hydrophilic agents upon an external trigger of a magnetic field gradient.

Methods

A. Hydrogel Matrix Preparation

Organic dye (Rhodamine B and Brilliant Green) was dissolved in water. In the dye water, a piece of clear, dried hydrogel was immersed overnight.

B. Vessel

Perfluoroalkoxy (PFA) tube with inner diameter of 0.559 mm and outer diameter of 1 mm was cut in 3 mm length. One end of the PFA tube was capped with epoxy and cured overnight. Once the epoxy was cured, a ferromagnetic, 440C stainless steel sphere (Bal-tec) of a diameter of 0.5 mm was inserted into the PFA tube. Subsequently, a matrix was loaded onto the vessel Finally, the mouth of the vessel was slightly clamped so that the minor axis of the inner diameter did not exceed 0.4 mm.

Results

Figure 1:
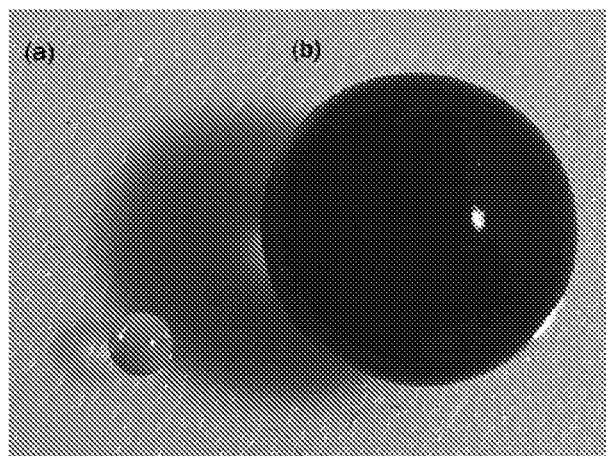
FIG. 1: (a) Dry, clear hydrogel before immersion in Rhodamine dissolved water. Diameter of the hydrogel sphere is measured to be 2.1 mm (b) The pellet's diameter increases to 10.1 mm as it absorbs Rhodamine B-dissolved water overnight.

FIG. 1 demonstrates changes in a hydrogel matrix before and after immersing them in Rhodamine B-dissolved water. Before immersion, dry hydrogel spherical pellet was clear and had a diameter of 2.1 mm, as demonstrated in FIG. 1(a). After soaking the pellet in Rhodamine B water overnight, the hydrogel soaked up the solution and expanded its diameter to 10.2 mm (FIG. 1(b)). This diameter increase, along with the color change from clear to deep red, indicate that they hydrogel pellets absorbed both water and Rhodamine B. This provides a platform where a water-soluble matrix can be integrated into a gel form for delivery.

Figure 2:
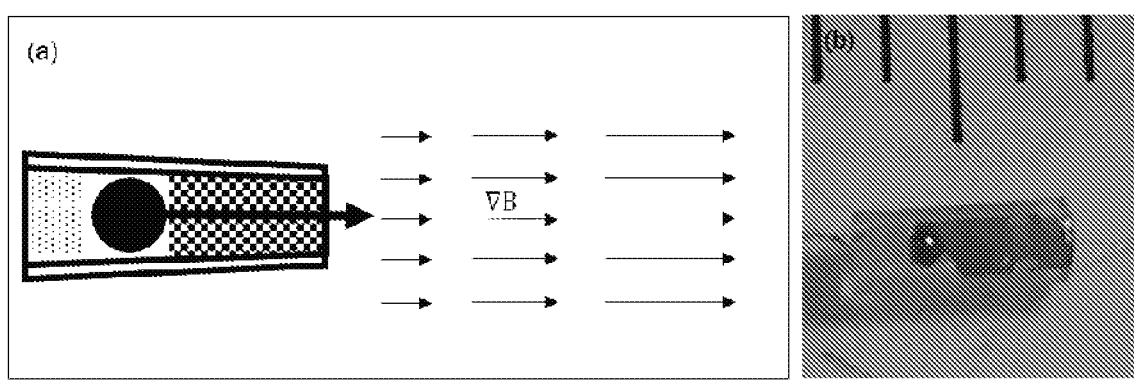
FIG. 2: (a) A schematic of the vessel and its mechanism. The dark lines indicate the boundaries of the PFA tube. The dotted region represents epoxy used to seal, the solid black sphere represents a ferromagnetic stainless-steel sphere, and the checkered region represents the matrix. In the presence of external magnetic gradient (denoted by thin arrows), the ferromagnetic sphere travels along the gradient, as denoted by a thick arrow. During this process, the ferromagnetic sphere pushes out the matrix. Deformed mouth prohibits the sphere from exiting the vessel. (b) A representative image of a vessel. Lefthand side of the tube is sealed with epoxy along with a 0.5 mm diameter stainless steel sphere, and the magenta colored gel is the matrix that is to be extruded from the vessel.

Once this dye-infused hydrogel matrix was prepared, it was loaded onto the vessel as described in the methods section. FIG. 2(a) is a schematic showing the final vessel and its mechanism In the presence of external magnetic gradient, the ferromagnetic stainless-steel piston travels in the direction of increasing gradient. In this process, the piston physically pushes out the hydrogel matrix. FIG. 2(b) is a representative image of a fabricated vessel. Roughly 1 mm thick clear layer present on the left-hand side is the epoxy used to seal one end of the vessel. Then a ferromagnetic stainless-steel sphere with a diameter of 0.5 mm was inserted into the vessel, followed by Rhodamine soaked hydrogel. The vessel mouth was then deformed with a clipper to prevent the piston from exiting the vessel.

Figure 3:
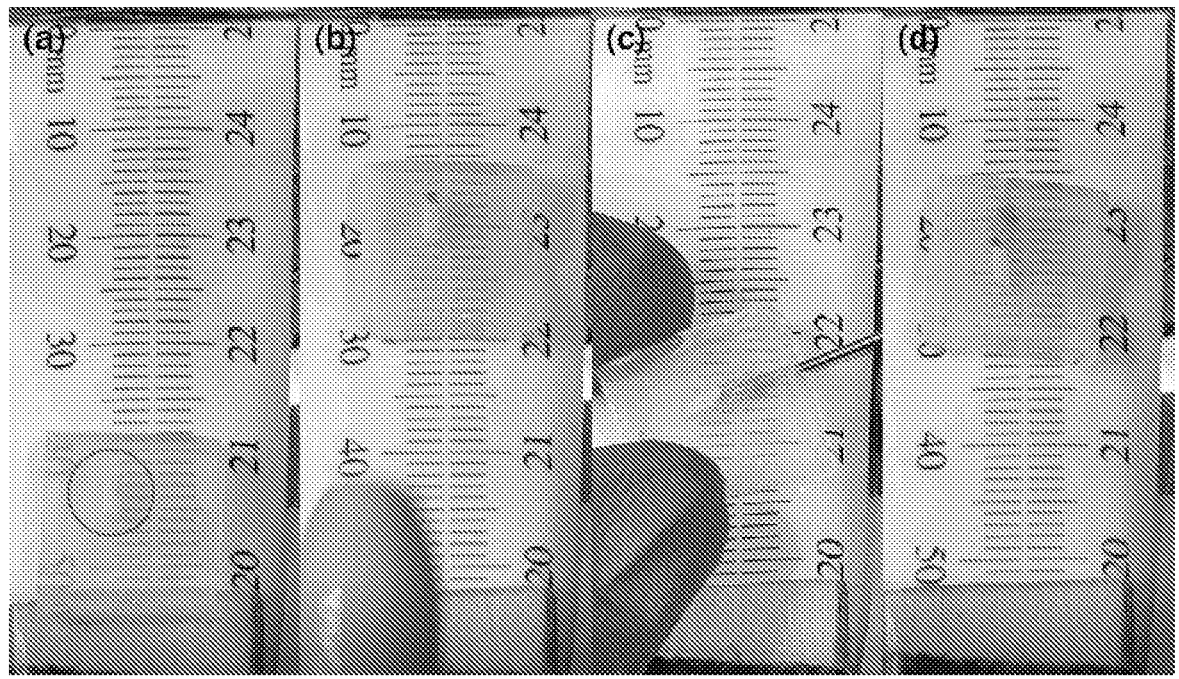
FIG. 3: Images demonstrating multiple releases of hydrogel soaked with Rhodamine B. (a) A vessel (highlighted by a red circle in the image) is embedded in a piece of agar gel.

The prepared vessel was inserted into a small piece of agar using a 20 G needle to minimize unnecessary damage to the surrounding medium, as depicted in FIG. 3(a). Once the vessel was embedded in agar, it was placed on a small stage perpendicular to a large magnet, and incrementally brought closer to the magnet while monitoring extrusion. When the vessel was brought close enough to the magnet (with magnetic field gradient ~15 T/m) extrusion of a small amount of hydrogel was visible, as demonstrated in FIG. 3(b). After the initial extrusion, the vessel was moved deeper into agar with a 20 G needle (FIG. 3(c)) to mimic bot's movement to a different location. When the agar embedded with the vessel was exposed to a large magnetic gradient of ~15 T/m, the remaining matrix was extruded from the vessel. This is evidenced by the red gel present at the mouth of the vessel in FIG. 3(d).

This mechanomagnetic concept demonstrated (1) fabrication of vessel loaded with a ferromagnetic piston and hydrogel matrix soaked in water-soluble agents, and (2) multiple extrusion of the hydrogel matrix in the presence of external magnetic field gradient of ~15 T/m. This opens up opportunities to design and fabricate millimeter-scale vessels that can release matrices multiple times upon application of external magnetic trigger, such as a field gradient.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A device for implanting in a biological tissue to release a functional material in said tissue or in another tissue, the device comprising:
    a cavity having an opening through an external surface of said device;
    a matrix comprising a functional material, wherein the matrix is contained within said cavity; and
    a magnetic component contained and moveable in said cavity, and is arranged so that, when a magnet trigger is applied, the magnetic component extrudes the matrix through the opening of cavity to be released into the tissue, and
    wherein the cavity is sealed by or covered with a flexible seal, which opens when the matrix is extruded by the magnetic component.

2. The device of claim 1, wherein the matrix is a hydrogel matrix.

3. The device of claim 1, wherein the matrix is a polycaprolactone, (poly)ethyleneglycols, glycinebetaine, alginates, collagen or collagen composites matrix.

4. The device of claim 1, wherein the magnetic trigger is selected from a magnetic gradient, uniform magnetic field changing its direction in space, presence/absence of a magnetic signal or a combination thereof.

5. The device of claim 1, further comprising a propelling component.

6. The device of claim 5, wherein said propelling component is responsive to external stimuli, and said stimuli are selected from ultrasound (US), magnetic, electric, electromagnetic, optical (e.g., near infrared (NIR)), electromagnetic radiation or a combination thereof, and wherein application of said stimuli to said propelling component propels said device.

7. The device of claim 6, wherein the external stimulus is magnetic and propels said device in a direction of propulsion.

8. The device of claim 7, wherein the cavity opening is in an opposite or orthogonal direction to the direction of propulsion.

9. The device of claim 7, wherein the propelling component and the moveable magnetic component are located at a predefined distance from each other to prevent interference via attraction.

10. The device of claim 7, wherein the propelling component and the moveable magnetic component are shielded to prevent interference via attraction by a magnetic shielding material.

11. The device of claim 1, wherein the flexible seal closes when the magnetic trigger is removed.

12. The device of claim 1, wherein the device has a plurality of cavities each having a matrix comprising a functional material and a magnetic component.

13. The device of claim 12, wherein the configuration of the plurality of cavities and each magnetic component is adapted so that payload release from each cavity can be controlled independently.

14. The device of claim 1, wherein the magnetic component comprises ferromagnetic stainless steel.

15. A system comprising:
    the device of claim 1; and
    a remote unit;
    wherein said remote unit is configured to apply external stimuli to said device.

16. The system of claim 15, wherein said external stimuli comprises:
    the magnetic trigger(s);
    magnetic/electric, electromagnetic or ultrasound (US) stimuli to propel the device; or
    a combination thereof.

17. A method of treating a subject, said method comprises:
    inserting the device of claim 1 into said subject;
    applying the magnetic trigger to said device to release the matrix in the subject.

18. The method of claim 17, wherein said inserting the device comprises inserting the device into a certain tissue within said subject.

19. The method of claim 18, after inserting the device into the tissue applying external stimuli to propel the device to a defined location within the subject.

20. The method of claim 19, wherein said external stimuli comprise ultrasound (US), magnetic, electric, electromagnetic, optical (e.g., near infrared (NIR)), electromagnetic radiation or a combination thereof.

21. The method of claim 17, wherein following the release of the matrix into the tissue, the functional material interacts the said tissue or with component(s) of/in the tissue.

22. The method of claim 21, wherein said interaction results in a therapeutic effect, a diagnostic effect or a combination thereof.

23. The method of claim 17, further comprising imaging the location of said device within said subject.

24. The method of claim 17, further repeating the application of the magnetic trigger, to repeat releasing the matrix in the biological tissue.

* * * * *